Figure 1:
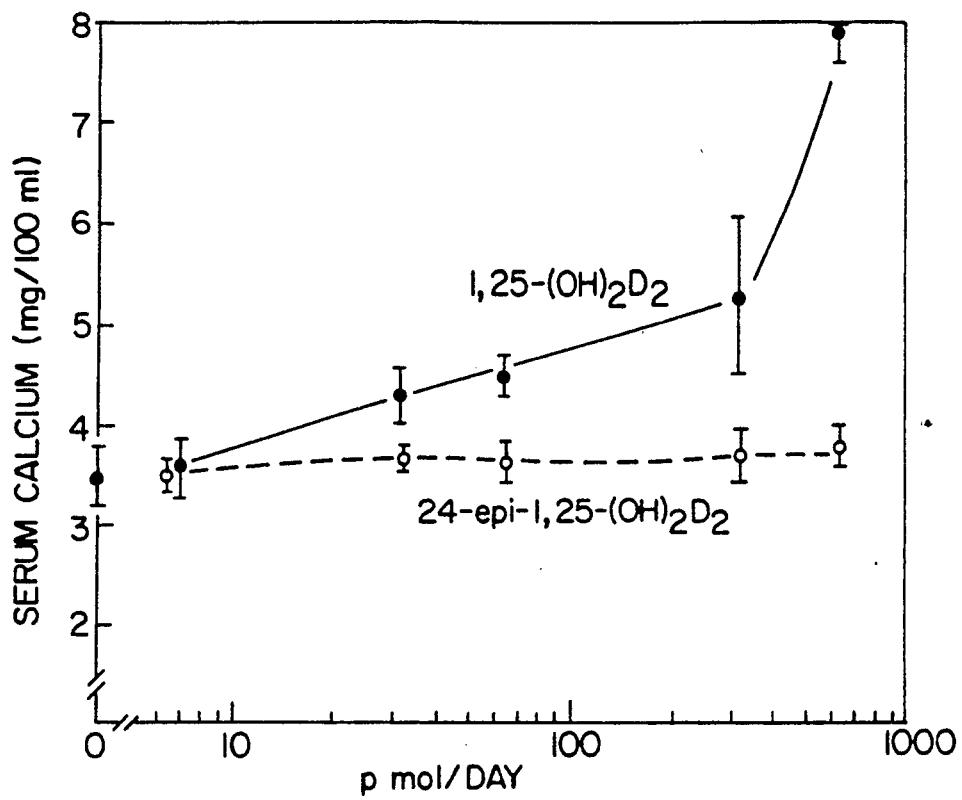

United States Patent [19]

DeLuca et al.

[11] Patent Number: 5,036,061
[45] Date of Patent: Jul. 30, 1991

[54] PROCESS FOR THE PREPARATION OF 1 ALPHA,25-DIHYDROXYLATED VITAMIN $D_2$ AND RELATED COMPOUNDS

[76] Inventors: Hector F. DeLuca, 5130 Minocqua Crescent; Heinrich K. Schnoes, 1806 Summit Ave., both of Madison, Wis. 53705; Rafal R. Sicinski, University of Warsaw, Department of Chemistry, 02-093, Warsaw, Pasteura 1, Poland; Yoko Tanaka, 72 Paxwood Rd., Delmar, N.Y. 12054

[21] Appl. No.: 442,483

[22] Filed: Nov. 22, 1989

Related U.S. Application Data

[63] Continuation of Ser. No. 862,075, May 12, 1986, abandoned, which is a continuation-in-part of Ser. No. 492,863, May 9, 1983, abandoned.

[51] Int. Cl.$^5$ .......................... A61K 31/59; C07J 9/00
[52] U.S. Cl. .................................... 514/167; 549/453; 540/116
[58] Field of Search ..................... 514/167; 260/397.2; 549/453

[56] References Cited

U.S. PATENT DOCUMENTS

| | | | |
|---|---|---|---|
| 4,225,596 | 9/1980 | DeLuca | 260/397.2 |
| 4,260,549 | 4/1981 | DeLuca et al. | 260/397.2 |
| 4,267,117 | 5/1981 | Salmond | 260/397.2 |
| 4,269,777 | 5/1981 | DeLuca et al. | 260/397.2 |
| 4,448,721 | 5/1984 | DeLuca et al. | 549/453 |

OTHER PUBLICATIONS

Salmond et al, Tetrahedron Letters, No. 20, pp. 1695–1698, 1977.

Master's Thesis "Structure Function Relationships of Synthetic and Natural Analogs of Vitamin D" by Lorraine E. Reere, 1977, pp. 78–95.

*Primary Examiner*—C. Warren Ivy
*Assistant Examiner*—Zinna Northington-Davis
*Attorney, Agent, or Firm*—Andrus, Sceales, Starke & Sawall

[57] ABSTRACT

The present invention provides novel derivatives of vitamin $D_2$ and more specifically 1 alpha,25-dihydroxylated compounds of the vitamin D series. A process for the preparation of such derivatives is also provided as are certain intermediates in such process.

The derivatives of this invention find ready application as substitutes for vitamin $D_3$ or $D_2$ or various of the known vitamin metabolites of these vitamins in their various applications to the correction of disorders involving calcium metabolism and associated bone disease.

16 Claims, 2 Drawing Sheets

PROCESS FOR THE PREPARATION OF 1 ALPHA,25-DIHYDROXYLATED VITAMIN D$_2$ AND RELATED COMPOUNDS

This application is a continuation of application Ser. No. 06/862,075, filed May 12, 1986, abandoned which in turn is a continuation-in-part of application Ser. No. 492,863, filed May 9, 1983 abandoned.

TECHNICAL FIELD

This invention relates to the preparation of 1 alpha,25-dihydroylated compounds of the vitamin D$_2$ series.

More specifically, this invention relates to the preparation of 1 alpha,25-dihydroxyvitamin D$_2$ and its (24R)-epimer, the corresponding 5,6-trans-isomers, and to certain C-25-alkyl or aryl analogs as well as the acyl derivatives of these compounds.

BACKGROUND

The importance of the hydroxylated forms of vitamin D as regulators of calcium and phosphate metabolism in animals and humans is by now well recognized through many disclosures in the patent and general literature. Vitamin D$_3$ is known to be hydroxylated in vivo to 25-hydroxyvitamin D$_3$ and then to 1 alpha,25-dihydroxyvitamin D$_3$, the latter being generally accepted as the active hormonal form of vitamin D$_3$. Similarly, the very potent vitamin D$_2$ metabolite, 1 alpha,25-dihydroxyvitamin D$_2$ (1 alpha,25-(OH)$_2$D$_2$) is formed from vitamin D$_2$ via 25-hydroxyvitamin D$_2$ (25-OH-D$_2$). Both of these hydroxylated vitamin D$_2$ compounds have been isolated and identified (DeLuca et al, U.S. Pat. Nos. 3,585,221; 3,880,894) and syntheses relating to hydroxyvitamin D$_2$ derivatives has also been reported (Sardina et al. Tet. Letters 24, 4477 (1983); DeLuca et al., U.S. Pat. No. 4,448,721; Yamada et al. Tet. Letters, 25, 3347 (1984); Baggiolini et al. U.S. Pat. No. 4,508,651; Morzycki et al. Journ. Org. Chem. 49, 2148 (1984)).

DISCLOSURE OF INVENTION

A chemical process for preparing 1 alpha,25-dihydroxylated compounds of the vitamin D$_2$ series has now been developed (Synthesis of 1 alpha,25-Dihydroxyvitamin D$_2$, Its 24 Epimer and Related Isomers, and Their Binding Affinity for the 1,25-Dihydroxyvitamin D$_3$ Receptor, Sicinski, Tanaka, Schnoes, DeLuca, Bioorganic Chemistry 13, 158–169 (1985)-Mailed June 3, 1985). Specifically, this process provides a convenient means for preparing compounds having the general structures A and B shown below,

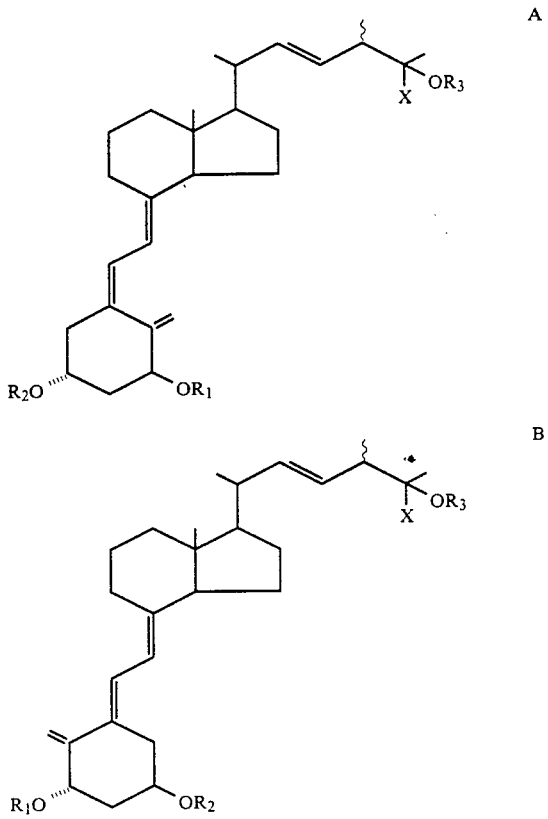

wherein R$_1$, R$_2$, and R$_3$ are selected from the group consisting of hydrogen and acyl, and where X is an alkyl or aryl group. In these structures the asymmetric center at carbon 24 may have the (R) or (S) configuration.

Specific examples of compounds obtainable by the present process include 1 alpha,25-dihydroxyvitamin D$_2$, the corresponding (24R)-epimer, 1 alpha,25-dihydroxy-24-epivitamin D$_2$, the respective 5,6-trans-isomers, i.e. 5,6-trans-1 alpha, 25-dihydroxyvitamin D$_2$, and 5,6-trans-1 alpha,25-dihydroxy-24-epivitamin D$_2$, as well as the C-25-alkyl or aryl homologs of these compounds, i.e. the compounds having the formulae shown above where X is ethyl, propyl, isopropyl or phenyl.

In this specification and in the claims the term "acyl" signifies an aliphatic acyl group (alkanoyl group) of from 1 to 6 carbons, in all possible isomeric forms, e.g. formyl, acetyl, butyryl, isobutyryl, valeryl, etc., or an aromatic acyl group (aroyl group) such as benzoyl, or the methyl, halo, or nitro-substituted benzoyl groups, or an acyl group derived from a dicarboxylic acid having the general formulae ROOC(CH$_2$)$_n$CO—, or ROOCH$_2$—O—CH$_2$CO—, where n is an integer having the values of 0 to 4 inclusive, and R is hydrogen or an alkyl radical. Representative of such dicarboxylic acyl groups are oxalyl, malonyl, succinoyl, glutaryl, adipyl and diglycolyl. The term "alkyl" refers to a hydrocarbon group of 1 to 6 carbons in all isomeric forms, e.g. methyl, ethyl, propyl, isopropyl, butyl, isobutyl, etc. The term "aryl" refers to an aromatic radical such as phenyl, benzyl, or the isomeric alkyl-substituted phenyl radicals.

An embodiment of the chemical process of this invention is depicted in appended Process Scheme I. In the following description of this process, numerals (e.g. 1, 2, 3, etc) designating specific products refer to the structures so numbered in Process Scheme I. A wavy line to the substituent (methyl) at C-24 indicates that this substituent may have either the R or S configuration.

A suitable starting material for the process of this invention is the vitamin D-ketal derivative of structure (1). It is generally convenient (e.g. in the case when both C-24-epimers of 1 alpha,25-dihydroxyvitamin $D_2$ compounds are desired) to use compound (1) as a mixture of the 24R and S epimers, separation of the individual 24R and S-epimers being accomplished at a later stage of the process. However, the pure 24S, or the pure 24R-epimer of (1) are equally suitable starting materials, whereby the former compound upon being processed through the indicated synthetic steps will provide the (24S)-1 alpha,25-dihydroxy product, whereas the latter, treated analogously, will yield the corresponding (24R)-1 alpha,25-dihydroxylated product.

Starting material (1) is converted to the desired 1 alpha-hydroxylated form via cyclovitamin D derivatives (DeLuca et al., U.S. Pat. Nos. 4,195,027 and 4,260,549). Thus, treatment of compound (1) with toluenesulfonyl chloride in the conventional manner yields the corresponding C-3-tosylate (2), which is solvolyzed in an alcoholic medium to produce the novel 3,5-cyclovitamin D derivative (3). Solvolysis in methanol yields the cyclovitamin of structure (3) where Z=methyl, whereas the use of other alcohols, e.g. ethanol, 2-propanol, butanol, etc., in this reaction provides the analogous cyclovitamin D compounds (3), where Z is an alkyl group derived from the alcohol, e.g. ethyl, isopropyl, butyl, etc. Allylic oxidation of intermediate (3) with selenium dioxide and a hydroperoxide yields the 1 alpha-hydroxy-analog of structure (4). Subsequent acetylation of compound (4) provides the 1-acetate of structure (5, $R_1$=acetyl). If desired, other 1-O-acylates (structure 5, where $R_1$=acyl, e.g. the formate, propionate, butyrate, benzoate, etc.) are prepared by analogous conventional acylation reactions. The 1-O-acyl derivative is then subjected to acid-catalyzed solvolysis. When this solvolysis is conducted in a solvent medium containing water, there is obtained the 5,6-cis-vitamin D intermediate of structure (6, $R_1$=acyl, $R_2$=H) and the corresponding 5,6-trans-compound (structure 7, $R_1$=acyl, $R_2$=H)) in a ratio of about 3-4:1. These 5,6-cis and 5,6-trans-isomers can be separated at this stage, e.g. by high performance liquid chromatography. If desired, the C-1-O-acyl group may be removed by base hydrolysis to obtain compounds (6) and (7) where $R_1$ and $R_2$=H. Also if desired, these 1-O-monoacylates may be further acylated at the C-3-hydroxy groups, using conventional acylation conditions to obtain the corresponding 1,3-di-O-acylates of structure (6) or (7) where $R_1$ and $R_2$, which may be the same or different, represent acyl groups. Alternatively, the hydroxy cyclovitamin of structure (4) can be subjected to acid-catalyzed solvolysis in a medium containing a low-molecular weight organic acid to obtain the 5,6-cis and trans compounds of structures (6) and (7) where $R_1$=H and $R_2$=acyl, where the acyl group is derived from the acid used in the solvolysis reaction.

The next step of the process comprises the removal of the ketal protecting group to produce the corresponding 25-ketone. This step is a critical one, since the ketal to ketone conversion must be accomplished without concomitant isomerization of the 22(23)-double bond to the conjugated 23(24)-position, which can occur under the acidic conditions required for ketal hydrolysis. Furthermore, conditions must be chosen so as to avoid elimination of the sensitive allylic C-1-oxygen function. The conversion is accomplished successfully by careful hydrolysis at moderate temperatures using organic acid catalysis. Thus, treatment of the 5,6-cis-compound (6) in aqueous alcohol with p-toluenesulfonic acid gives the corresponding ketone (8). To avoid undesired elimination of the C-1-oxygen function during this reaction, it is advantageous that the C-1-hydroxy group in compound (6) be protected (e.g. $R_1$=acyl, $R_2$=hydrogen or acyl).

Subsequent reaction of ketone (8) with a methyl-Grignard reagent then provides the desired 1 alpha,25-dihydroxyvitamin $D_2$ compound of structure (9). If the starting material, compound (1), used in the above process, is a mixture of the two C-24-epimers, then compound (9) will be obtained as a mixture of the 24S and R-epimers (9a and 9b, respectively). Separation of this epimer mixture can be achieved by chromatographic methods, to obtain 1 alpha,25-dihydroxyvitamin $D_2$ (structure 9a, 24S-stereochemistry) and its 24R-epimer, 1 alpha,25-dihydroxy-24-epivitamin $D_2$, of structure 9b, both in pure form. Such separation of epimers is, of course, not necessary if the compounds are intended to be used as a mixture.

The 5,6-trans-25-ketal-intermediate of structure (7), subjected to ketal hydrolysis in an analogous manner, provides the 5,6-trans ketone intermediate of structure (10), which via a Grignard reaction with methyl magnesium bromide or analogous reagent gives the 5,6-trans-1 alpha,25-dihydroxyvitamin $D_2$ compounds of structure (11), as the 24S or 24R-epimer, or as a mixture of both epimers depending on the nature of the starting material (1) used in the process. If obtained as an epimeric mixture, the epimers can be separated by chromatography, to obtain 5,6-trans-1 alpha,25-dihydroxyvitamin $D_2$ (11a) and its 24R-epimer, 5,6-trans-1 alpha,25-dihydroxy-24-epivitamin $D_2$, of structure (11b). These reaction steps utilizing the 5,6-trans-intermediate are conducted in a manner entirely analogous to those applicable to the 5,6-cis-compounds described above.

The novel side chain ketones of structures (8) or (10) are most useful and versatile intermediates in that they can be used to prepare a variety of 1 alpha,25-dihydroxyvitamin $D_2$ -side chain analogs. Specifically, these keto-intermediates can serve for the preparation of 5,6-cis- or 5,6-trans-1,25-dihydroxyvitamin $D_2$ analogs having the general side chain formula shown below,

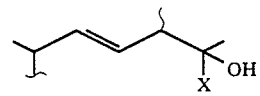

where X is an alkyl or aryl group.

For example, treatment of ketone (8) with ethyl magnesium bromide gives the corresponding hydroxyvitamin $D_2$ analog having the side chain structure shown above wherein X is ethyl group. Likewise, treatment of (8) with isopropyl magnesium bromide or phenyl magnesium bromide gives the side chain analogs where X is isopropyl or phenyl, respectively. Analogous treatment of the 5,6-trans-25-ketone intermediate of structure (10) with alkyl or aryl-Grignard reagents gives the 5,6-trans-vitamin $D_2$ analog having the side chain above where X is the alkyl or aryl radical introduced by the Grignard reagent employed.

It is also evident that the reaction of the keto-intermediates (8) or (10) with an isotopically-labeled Grignard reagent (e.g. $C^3H_3MgBr$, $^{14}CH_3MgBr$, $C^2H_3MgBr$, etc.) provides a convenient means for preparing 1 alpha,25-dihydroxyvitamin $D_2$ or its trans isomer, and the corresponding C-24-epimers, in isotopically-labeled form, i.e. as the compounds having the side chain shown above, wherein X is $C^3H_3$, $^{14}CH_3$, $C^2H_3$, $^{13}CH_3$, or any other isotopically-labeled alkyl or aryl group selected.

The above alkyl or aryl homologues of the 5,6-cis or trans-1 alpha,25-dihydroxy-vitamin $D_2$ are useful substitutes of the parent compounds in situations where a greater degree of lipophilicity is desired, whereas the isotopically labeled compounds referred to above, find use as reagent in analytical applications.

Further, although for therapeutic applications, the free hydroxy compounds represented by structures A and B above (where $R_1$, $R_2$ and $R_3$=H) are generally used, for some such applications, the corresponding hydroxy-protected derivatives may be useful or preferred. Such hydroxy-protected derivatives are for example the acylated compounds represented by general formulae A and B above, wherein one or more of $R_1$, $R_2$, and $R_3$ represents an acyl group.

Such acyl derivatives are conveniently prepared from the free hydroxy compounds by conventional acylation procedures, i.e. treatment of any of the hydroxyvitamin $D_2$ products with an acyl halide, or acid anhydride in a suitable solvent such as pyridine, or an alkyl-pyridine. By appropriate selection of reaction time, acylating agent, temperature and solvent, as is well-known in the art, the partially or fully acylated derivatives represented by structures A or B above are obtained. For example, treatment of 1 alpha,25-dihydroxyvitamin $D_2$ (9a) in pyridine solvent with acetic anhydride at room temperature gives the 1,3-diacetate, while the same reaction conducted at elevated temperature yields the corresponding 1,3,25-triacetate. The 1,3-diacetate can be further acylated at C-25 with a different acyl group; e.g. by treatment with benzoyl chloride or succinic anhydride there is obtained the 1,3-diacetyl-25-benzoyl-, or 1,3-diacetyl-25-succinoyl-derivative, respectively. A 1,3,25-triacyl derivative can be selectively hydrolyzed in mild base to provide the 1,3-dihydroxy-25-0-acyl compound, the free hydroxy groups of which can be reacylated, if desired, with different acyl groups. Likewise, a 1,3-diacyl derivative can be subjected to partial acyl hydrolysis to obtain the 1-0-acyl and the 3-0-acyl compounds, which in turn can be reacylated with different acyl groups. Like treatment of any of the other hydroxyvitamin $D_2$ products (e.g. 9b, 11a/b, or their corresponding 25-alkyl or aryl analogs) provides the corresponding desired acyl derivatives represented by structures A or B, where any or all of $R_1$, $R_2$, and $R_3$ are acyl.

The process of the present invention is more particularly described by Examples 1 through 7 which follow. In these examples the designation of specific products by Arabic numerals (e.g. compounds 1, 2, 3, etc.) refer to the structures so numbered in Process Scheme I.

EXAMPLE 1

1 alpha-hydroxy-3,5-cyclovitamin D (4, Z=methyl)

A solution of compound (1) (50 mg) (as a mixture of the 24R and S epimers) in dry pyridine (300 μl) is treated with 50 mg of p-toluenesulfonyl chloride at 4° C. for 30 h. The mixture is poured over ice/sat. NaHCO₃ with stirring and the product is extracted with benzene. The combined organic phases are washed with aqueous $NaHCO_3$, $H_2O$, aqueous $CuSO_4$ and water, dried over $MgSO_4$ and evaporated.

The crude 3-tosyl derivative (2) is directly solvolyzed in anhydrous methanol (10 ml) and $NaHCO_3$ (150 mg) by heating at 55° C. for 8.5 h with stirring. The reaction mixture is then cooled to room temperature and concentrated to 2 ml under vacuo. Benzene (80 ml) is then added and organic layer is washed with water, dried and evaporated. The resulting cyclovitamin (3, Z=methyl) can be used in the subsequent oxidation without further purification.

The crude product (3) in $CH_2Cl_2$ (4.5 ml) is added to an ice-cooled solution at $SeO_2$ (5.05 mg) and t-BuOOH (16.5 μl) in $CH_2Cl_2$ (8 ml) containing anhydrous pyridine (50 μl). After being stirred for 15 min at 0° C., the reaction mixture is allowed to warm to room temperature. After an additional 30 min, the mixture is transferred to a separatory funnel and shaken with 10% NaOH (30 ml). Ether (150 ml) is added and the separated organic phase is washed with 10% NaOH, water, dried and evaporated. The oily residue is purified on silica gel thin layer plates (20×20 cm plates, AcOEt/hexane 4:6) to yield 20 mg of 1 alpha-hydroxy derivative (4, Z=methyl): mass spectrum, m/e: 470 (M+, 5), 438 (20), 87 (100); NMR (CDCl₃) δ0.53 (3H, s, 18-H₃), 0.63 (1H, m, 3-H), 4.19 (1H, d, J=9.5 Hz, 6-H), 4.2 (1H, m, 1-H), 4.95 (1H, d, J=9.5 Hz, 7-H), 5.17 and 5.25 (2H, each m, 19-H₂), 5.35 (2H, m, 22-H and 23-H).

EXAMPLE 2

Acetylation of compound (4)

A solution of cyclovitamin (4, Z=methyl) (18 mg) in pyridine (1 ml) and acetic anhydride (0.33 ml) is heated at 55° C. for 2 h. The mixture is poured into ice-cooled sat. NaHCO₃ and extracted with benzene and ether. The combined organic extracts are washed with water, saturated $CuSO_4$ and aqueous $NaHCO_3$ solutions, dried and evaporated to give 1-acetoxy derivative (5, Z=methyl, acyl=acetyl) (19 mg): mass spectrum, m/e: 512 (M+, 5), 420 (5), 87 (100); NMR (CDCl₃) δ0.53 (3H, s, 18-H₃), 4.18 (1H, d, J=9.5 Hz, 6-H), 4.97 (2H, m, 7-H and 19-H), 5.24 (2H, m, 1-H and 19-H), 5.35 (2H, m, 22-H and 23-H).

EXAMPLE 3

Solvolysis of 1 alpha-acetoxy-3,5-cyclovitamin (5) ($R_1$=acetyl)

A solution of cyclovitamin (5) (4.5 mg) in 3:1 mixture of dioxane/H₂O (1.5 ml) is heated at 55° C. p-Toluenesulfonic acid (1 mg in 20 l of H₂O) is then added and heating is continued for 15 min. The mixture is poured into saturated NaHCO₃/ice, and extracted with benzene and ether. The organic phases are washed with NaHCO₃ and water and dried over MgSO₄. Evaporation of solvents gives a residue containing compounds (6) (where $R_1$=acetyl and $R_2$=H) and (7) (where $R_1$=acetyl and $R_2$=H) which are separated by chromatography on HPLC (6.2 mm×25 cm Zorbax-Sil) using 2% of 2-propanol in hexane as an eluent. If necessary, the products are further purified by rechromatography.

EXAMPLE 4

Ketal hydrolysis in compound (6) to obtain ketone (8)

To the solution of ketal (6, $R_1$=acetyl, $R_2$=H) (1.35 mg) in ethanol (1.5 ml), p-toluenesulfonic acid (0.34 mg in 45 μL of $H_2O$) is added and the mixture is heated under reflux for 30 min. The reaction mixture is poured into diluted $NaHCO_3$, and extracted with benzene and ether. The combined organic extracts are washed with water, dried over $MgSO_4$ and evaporated. High-pressure liquid chromatography of the crude mixture (4% 2-propanol/hexane, 6.2 mm×25 cm Zorbax-Sil) affords some unreacted ketal (6) (0.12 mg, collected at 48 ml) and desired ketone (8, $R_1$=acetyl, $R_2$=H) (0.36 mg, collected at 52 ml), characterized by the following data: mass spectrum, m/e: 454 ($M^+$, 9), 394 (17), 376 (10), 134 (23), 43 (100); NMR ($CDCl_3$) δ0.53 (3H, s, 18-$H_3$), 1.03 (3H, d, J=6.5 Hz, 21-$H_3$), 1.13 (3H, d, J=7.0 Hz, 28-$H_3$), 2.03 (3H, s, $CH_3COO$), 2.12 (3H, s, $CH_3CO$), 4.19 (1H, m, 3-H), 5.03 (1H, m, 19-H), 5.33 (3H, broad m, 19-H, 22-H and 23-H), 5.49 (1H, m, 1-H), 5.93 (1H, d, J=11 Hz, 7-H), 6.37 (1H, d, J=11 Hz, 6-H); UV (EtOH) $\lambda_{max}$ 266 nm, 250 nm, $\lambda_{min}$ 225 nm.

EXAMPLE 5

Reaction of ketone (8) with methylmagnesium bromide to obtain products (9a) and (9b)

Ketone (8, $R_1$=acetyl, $R_2$=H) in anhydrous ether is treated with the excess of $CH_3MgBr$ (2.85M solution in ether). The reaction mixture is stirred at room temperature for 30 min, then quenched with aq. $NH_4Cl$, extracted with benzene, ether and $CH_2Cl_2$. The organic phases are washed with dilute $NaHCO_3$, dried over $MgSO_4$ and evaporated. The mixture of (9a) (9b) thus obtained is separated by high performance liquid chromatography (6% 2-propanol/hexane, 4.6 mm×25 cm Zorbax-Sil), to obtain, in order of elution, pure epimers (9a) and (9b). 1 alpha,25-dihydroxyvitamin $D_2$ (9a): UV (EtOH) $\lambda_{max}$ 265.5 nm, $\lambda_{min}$ 227.5 nm; mass spectrum, m/e 428 ($M^+$, 6), 410 (4), 352 (4), 287 (6), 269 (10), 251 (10), 152 (42), 134 (100), 59 (99); NMR ($CDCl_3$) δ0.56 (3H, s, 18-$H_3$), 1.01 (3H, d, J=6.5 Hz, 28-$H_3$), 1.04 (3H, d, J=6.5 Hz, 21-$H_3$), 1.14 and 1.18 (6H, each s, 26-$H_3$ and 27-$H_3$), 4.24 (1H, m, 3-H), 4.43 (1H, m, 1-H), 5.01 (1H, m, 19-H), ~5.34 (3H, broad m, 19-H, 22-H and 23-H), 6.02 (1H, d, J=11 Hz, 7-H), 6.39 (1H, d, J=11 Hz, 6-H). 1 alpha,25-dihydroxy-24-epivitamin $D_2$ (9b): UV (EtOH) $\lambda_{max}$ 265.5 nm, $\lambda_{min}$ 227.5 nm; mass spectrum, m/e 428 ($M^+$, 13), 410 (9), 352 (7), 287 (11), 269 (15) 251 (13), 152 (52), 134 (100), 59 (97).

EXAMPLE 6

Conversion of compound (7) to 5,6-trans-1 alpha, 25-dihydroxyvitamin $D_2$ compounds (11a) and (11b)

Hydrolysis of ketal-intermediate (7, $R_1$=acetyl, $R_2$=H) using the conditions described in Example 4 provides the corresponding 5,6-trans-25-ketone of structure (10, $R_1$=acetyl, $R_2$=H), and subsequent reaction of this ketone with methyl magnesium bromide, using conditions analogous to those of Example 5, gives a mixture of epimers (11a) and (11b) which are separated by high performance liquid chromatography (HPLC) to obtain in pure form 1 alpha,25-dihydroxy-5,6 -trans-vitamin $D_2$ (11a) and 1 alpha,25-dihydroxy -5.6-trans-24-epivita-min $D_2$(11b). If required, structure assignment can be confirmed by isomerization to the respective 5,6 cis compounds (9a, 9b) according to known procedures.

5,6-trans-1 alpha,25-dihydroxyvitamin $D_2$ (11a): UV (EtOH) $\lambda_{max}$ 273.5 nm, $\lambda_{min}$ 230 nm; mass spectrum, m/e 428 ($M^+$, 8), 410 (3), 287 (3), 269 (7), 251 (7), 152 (34), 134 (100), 59 (78).

5,6-trans-1 alpha,25-dihidroxy-24-epivitamin $D_2$ (11b): UV (EtOH) $\lambda_{max}$ 273.5 nm, $\lambda_{min}$ 230 nm; mass spectrum, m/e 428 ($M^+$, 10), 410 (4), 352 (4), 287 (5), 269 (9), 251 (8), 152 (37), 134 (100), 59 (82).

EXAMPLE 7

Preparation of alkyl and aryl analogs of 1 alpha, 25-dihydroxyvitamin $D_2$ compounds By reaction of ketone intermediate (8) ($R_1$=acetyl, $R_2$=H) with, respectively, (a) ethyl magnesium bromide
(b) propyl magnesium bromide
(c) isopropyl magnesium bromide
(d) butyl magnesium bromide
(e) phenyl magnesium bromide using conditions analogous to those described in Example 5, there are obtained the corresponding hydroxyvitamin $D_2$ products having the formula shown below

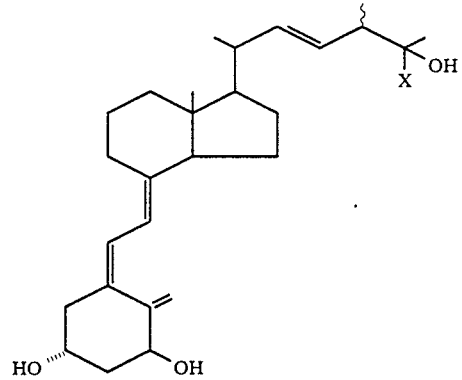

wherein X is, respectively (a) ethyl
(b) propyl
(c) isopropyl
(d) butyl
(e) phenyl By like treatment of 5,6-trans-ketone intermediate (10) ($R_1$=acetyl, $R_2$=H) with the above listed Grignard reagents, there are obtained the corresponding 5,6-trans-hydroxyvitamin $D_2$ products, having the formula shown below

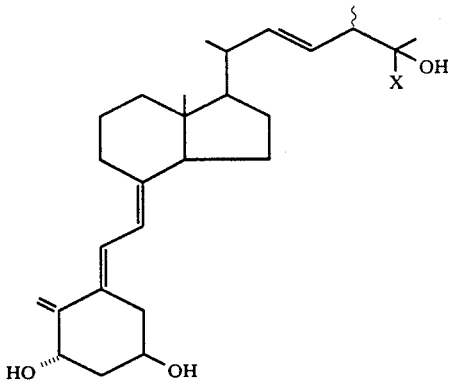

wherein X is, respectively
(a) ethyl
(b) propyl
(c) isopropyl
(d) butyl
(e) phenyl Preparation of Starting Material The starting material (compound 1 of Process Scheme I) required for the above described preparation of 1 alpha, 25-dihydroxyvitamin $D_2$ compounds can be obtained by the process shown in U.S. Pat. No. 4,448,721 as depicted in Process Schemes II and III, and as more particularly described by Examples 8 through 14 below. In these examples, compound designations by Arabic numerals (e.g. 1, 2, 3, etc.) refer to the structures so numbered in appended Process Scheme II.

EXAMPLE 8

The C-22 aldehyde (1) is obtained by degradation of ergosterol acetate (in which the ring B diene system has been protected by Diels-Alder addition of 4-phenyl-1, 2, 4-triazoline-3,5-dione) according to the procedure of Barton et al., J. Chem. Soc. (C) 1968 (1971). The i-ether aldehyde (4) is obtained from stigmasterol by the method of U.S. Pat. No. 2,623,052.

EXAMPLE 9

Synthesis of the Side Chain Fragment (Sulfone A, Process Scheme III appended)

To a stirred solution of 4-hydroxy-3-methylbutan-2-one (12.75 g; 0.125 mol) in pyridine (100 ml) is added p-toluenesulfonyl chloride (p-TsCl) (33.25 g, 0.175 mol) in portions, and after standing for 14 h at room temperature, the reaction mixture is poured into water and extracted with $CH_2Cl_2$. The extract is washed several times with aqueous $CuSO_4$ solution and water and then dried over anhydrous sodium sulfate. Removal of solvent under reduced pressure gives the crude tosylate which is used directly for the next reaction.

Thiophenol (14 g) dissolved in DMF (100 ml) is treated with t-BuOK (14 g). To this reagent, the tosylate is added and after 12 h at room temperature, the reaction mixture is poured into water and extracted with $CH_2Cl_2$. The extract is washed with aqueous $Na_2CO_3$ solution and water, then dried. Evaporation of solvent gives an oily residue which is purified by silica gel column chromatography. Pure phenyl sulfide is eluted with benzene (yield 15 g).

To this phenyl sulfide derivative (15 g), in benzene (100 ml), ethylene glycol (6 g) and p-TsOH (20 mg) is added and the reaction mixture is heated under a Dean-Stark trap for 3 h. After cooling, it is washed with $Na_2CO_3$ solution and water, then dried and the solvent is evaporated. The product, the desired ketal, is chromatographically homogenous and can be used in the next step without further purification.

Crude ketal in dichloromethane (250 ml) solution is treated with m-chloroperbenzoic acid (m-CPBA) (80–85%, 27 g, added in portions) while maintaining the temperature of the reaction mixture below 30° C. After the addition of reagent, the reaction is allowed to stand at room temperature with occasional shaking. When the reaction reaches completion (about 1.5 h), the aromatic acids are removed by extraction with aqueous $NH_3$, and the organic layer is washed with water and dried. Evaporation of solvent gives the oily sulfone (sulfone A) in essentially quantitative yield (19 g). The product is substantially pure (homogenous by TLC) and can be used without any further purification; $^1$H-NMR; $\delta$; 1.18 (d, J=7 Hz, 3H, $CH_3$—CH—), 1.19 (s, 3H), 3.84 (m, 4H, ketal-H), 7.3–7.6 and 7.6–7.9 (m, 3H=2H, aromatic protons): IR,$\nu KBr_{max}$ 1305,1147,1082 cm$^{-1}$; mass spectrum, m/z (rel. intensity): 255 (M$^+$-Me, 21), 184 (66), 87 (92), 43 (100).

EXAMPLE 10

Coupling of Sulfone A to Aldehyde (1): Hydroxysulfone (2) and Olefin (3).

Grignard reagent is prepared from Mg (535 mg; 22.22 mmol) and ethyl bromide in ether (10 ml), and the vigorously stirred solution is treated with sulfone A (6 g; 22.22 mmol) in benzene (6 ml). The precipitate formed is ground with a spatula, stirring is continued, and after 15 min the aldehyde (1) (2.0 g) is added in benzene (10 ml). The reaction mixture is stirred at room temperature for 24 h, then poured into aqueous $(NH_4)_2SO_4$ solution and extracted with benzene. The organic layer, after washing with water, drying and evaporation gives an oily residue which is chromatographed on silica gel. In the benzene-ether fractions (8:2), excess sulfone is recovered (4.5 g); elution with benzene-ether (3:1) affords unreacted aldehyde (1) (1.0 g); the reaction products (2) are eluted with ethyl acetate.

The crude mixture of steroidal alpha-hydroxysulfones (2) is dissolved in methanol (200 ml) saturated with $Na_2HPO_4$. Sodium amalgam (5.65%, 15 g) is added and the reaction mixture is stirred at 4° C. for 15 h.

After completion of the Na/Hg reduction, mercury is removed by filtration, and methanol by evaporation under reduced pressure, water is added and the organic material is extracted with benzene. After drying and evaporation of solvent, the oily residue is chromatographed on a silica gel column. Elution with benzene-ether (1:4) gives compound (3) a colorless foam; $^1$H-NMR, $\delta$: 0.80 (s, 18-H), 0.97 (s, 19-H), 1.22 (s, 26-H), 3.93 (m, 4H, ketal-H), 4.44 (m, 1H, 3 -H), 5.25–5.45 (m, 2H, 22-H and 23-H), 6.23 and 6.39 (doublets, J=8 Hz, 2×1H, 7-H and 6-H), 7.25–7.45 (m, 5H, —$C_6H_5$); IR, $CHCl_{max}3$: 3603 (0-H), 1749, 1692 (C=0), 1406,1038 cm$^{-1}$; mass spectrum, m/z: 440 (M$^+$-triazoline, 24), 87 (100).

(To increase yield, unreacted aldehyde (1), as recovered above, can be recycled through the sulfone addition, and the resulting alpha-hydroxy sulfones (2) are then, as above, treated with sodium amalgam in buffered methanol to provide additional olefin (3). The above reactions are preferably conducted under an inert atmosphere, such as argon.)

EXAMPLE 11

Coupling of Sulfone A to Aldehyde (4): Hydroxysulfone (5) and Olefin (6).

Grignard reagent is prepared from Mg (75 mg, 3.1 mmol) and ethyl bromide in ether (10 ml). To the stirred solution of ethyl magnesium bromide, sulfone A (891 mg; 3.3 mmol) in benzene (5 ml) is added. After stirring the resulting suspension at room temperature for 15 min, a solution of aldehyde (4) (290 mg) in benzene (5 ml) is added. The reaction is continued for 2.5 h, then quenched with saturated $(NH_4)_2SO_4$ solution (5 ml) and diluted with ether. The separated organic layer is washed with water, dried, and evaporated. The oily residue containing (5) is treated with acetic anhydride (2 ml) and pyridine (2 ml). The reaction mixture is allowed to stand for 24 h, poured into water and extracted with benzene. The benzene extract is washed with an aqueous solution of $CuSO_4$, water, dried, and evaporated. The crude product [the acetate of (5)] is dissolved in methanol saturated with $Na_2HPO_4$ and sodium amalgam (5.65%, 8 g) is added. The reaction mixture is stirred at 4° C. for 16 h. After the reaction, mercury is removed by filtration, methanol is evaporated, and water and benzene are added to dissolve the residue. The benzene layer is dried and evaporated. The oily residue is chromatographed over silica gel. Elution with benzene-ether mixture (93:7) affords compound (6) (206 mg; 54%), $^1$H-NMR, δ: 0.74 (s, 18-H), 1.04 (s, 19-H), 1.25 (s, 26-H), 2.78 (m, 1H, 6-H), 3.34 (s, 3H, —OCH$_3$), 3.97 (m, 4H, ketal-H), 5.25–5.45 (m, 2H, 22-H and 23-H), IR,$v_{max}^{KBr}$: 3470 (0-H), 1094 cm$^{-1}$; mass spectrum, m/z (rel. intensity): 456 (M+, 1), 441 (M+-Me, 45), 87 (100). It should be noted that the acetylation step described above is not essential and may be omitted if desired; i.e. the hydroxysulfone (5) may be submitted directly to Na/Mg-reduction, as in Example 3. The above reactions are preferably conducted under an inert atmosphere, e.g. argon.

EXAMPLE 12

Removal of PTAD-protecting Group: 5,7-Diene (7)

A mixture of the compound (3) (1 g) and lithium aluminum hydride (1.8 g) in THF (120 ml) is heated under reflux for 10 h. After cooling, excess reagent is destroyed with a few drops of water, and the mixture is dried over anhydrous MgSO$_4$, filtered, and solvent is evaporated to give colorless crystalline material. Crude diene 7 is repeatedly crystallized from ethanol; first and second crops combined give 415 mg of (7). The mother liquor is chromatographed on silica gel column, to give with benzene-ether (7:3), an additional 120 mg of (7); total yield 535 mg (79%); m.p. 132°–134° C. (from ethanol), $^1$H-NMR, δ: 0.63 (s, 18-H), 0.95 (s, 19-H), 1.23 (s, 26-H), 3.63 (m, 1H, 3-H), 3.95 (m, 4H, ketal-H), 5.20–5.50 (m, 3H, 22-H, 23-H and 7-H), 5.57 (s, 1H, 6-H); IR,$v_{max}^{KBr}$: 3430 (0-H), 1063, 1038 cm$^{-1}$; mass spectrum, m/z (rel. int.): 440 (M+, 50), 407 (M+-H$_2$O-Me, 11), 87 (100); UV,$\lambda_{max}^{EtOH}$: 282 nm (=11,000).

EXAMPLE 13

Irradiation of Compound (7): Previtamin Analog (8)

A solution of diene (7) (50 mg) in 150 ml of benzene-ether (1:4) is cooled on ice and deoxygenated with argon for 20 min. The reaction mixture is irradiated under argon atmosphere for 18 min with a mercury arc lamp (Hanovia SA-1) fitted with a Vycor filter. The solvent is evaporated and the residue is chromatographed on HPLC (6.2 mm×25 cm microparticulate silica gel, 4 ml/min, 1400 psi) and eluted with 2% 2-propanol in hexane to yield 22 mg (44%) of previtamin (8); $^1$H-NMR; δ: 0.73 (s, 18-H), 1.24 (s, 26-H), 1.64 (s, 19-H), 3.96 (m, 5H, ketal-H and 3-H), 5.35 (m, 2H, 22-H and 23-H), 5.50 (m, 1H, 9-H), 5.69 and 5.94 (doublets, J=11.5 Hz, 2×1H, 6-H and 7-H); UV, $\lambda_{max}^{EtOH}$: 263 nm (ε=8,900).

EXAMPLE 14

Isomerization of (8) to the Vitamin-Analog (9)

Previtamin 8 (22 mg) is dissolved in ethanol (40 ml) and heated under reflux for 150 min (argon atmosphere). The product is purified by HPLC to yield 18 mg (82%) of the pure vitamin-ketal (9); $^1$H-NMR, δ: 0.57 (s, 18-H), 1.24 (s, 26-H), 3.94 (m, 5H, ketal-H and 3-H), 4.81 and 5.04 (2 narrow m, 2×1H, 19(Z)- and 19(E)-H), 5.33 (m, 2H, 22-H and 23-H), 6.03 (d, J=11 Hz, 1H, 7-H), 6.22 (d, J=11 Hz, 1H, 6-H); mass spectrum, m/z (rel. int.): 440 (M+, 17), 87 (100), UV, $\lambda_{max}^{EtOH}$: 265 nm (ε=17,000). The product so obtained (compound 9) is used as the starting material for the process depicted in Process Scheme I, where this same material is identified as compound (1).

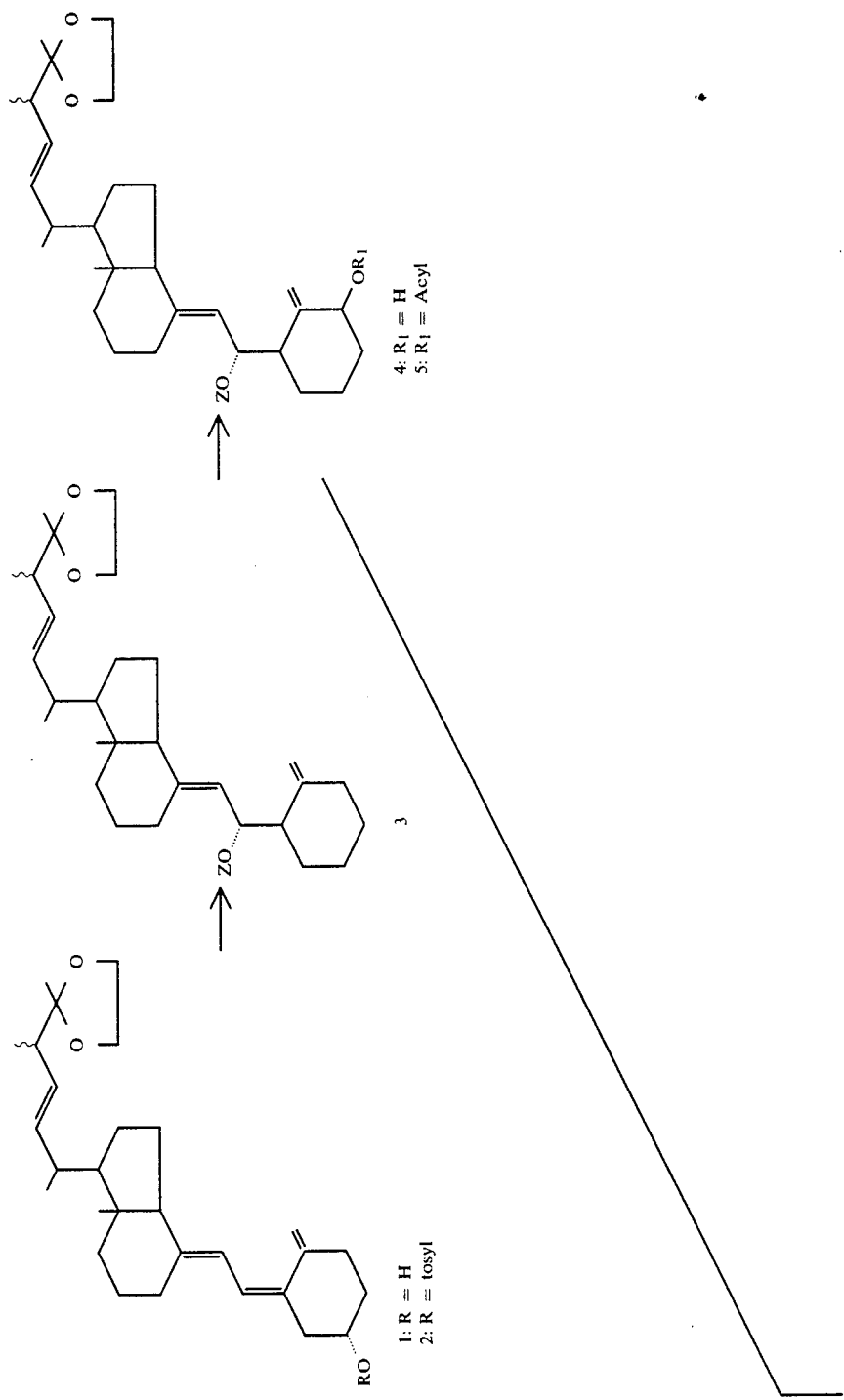

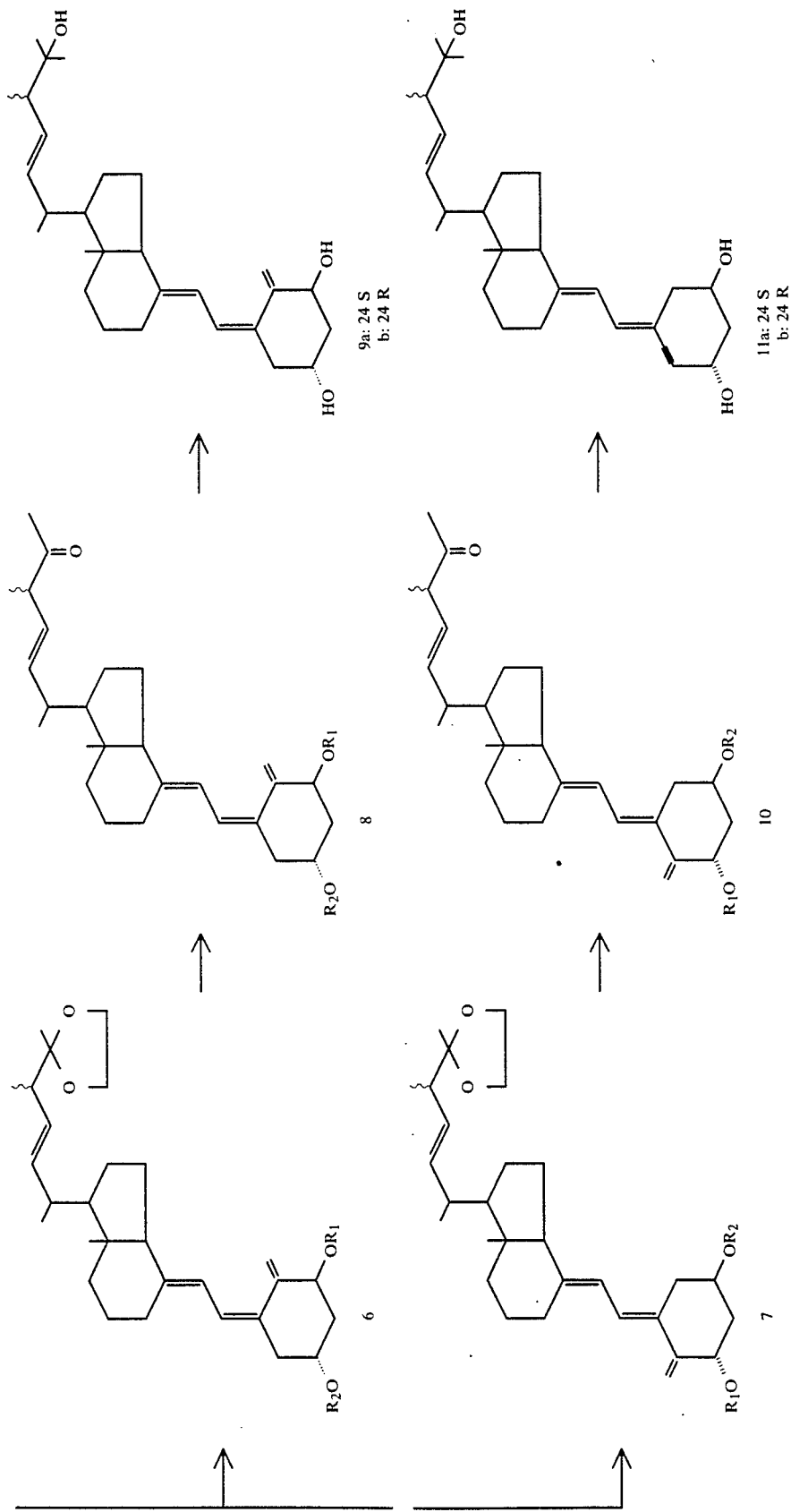

Process Scheme II
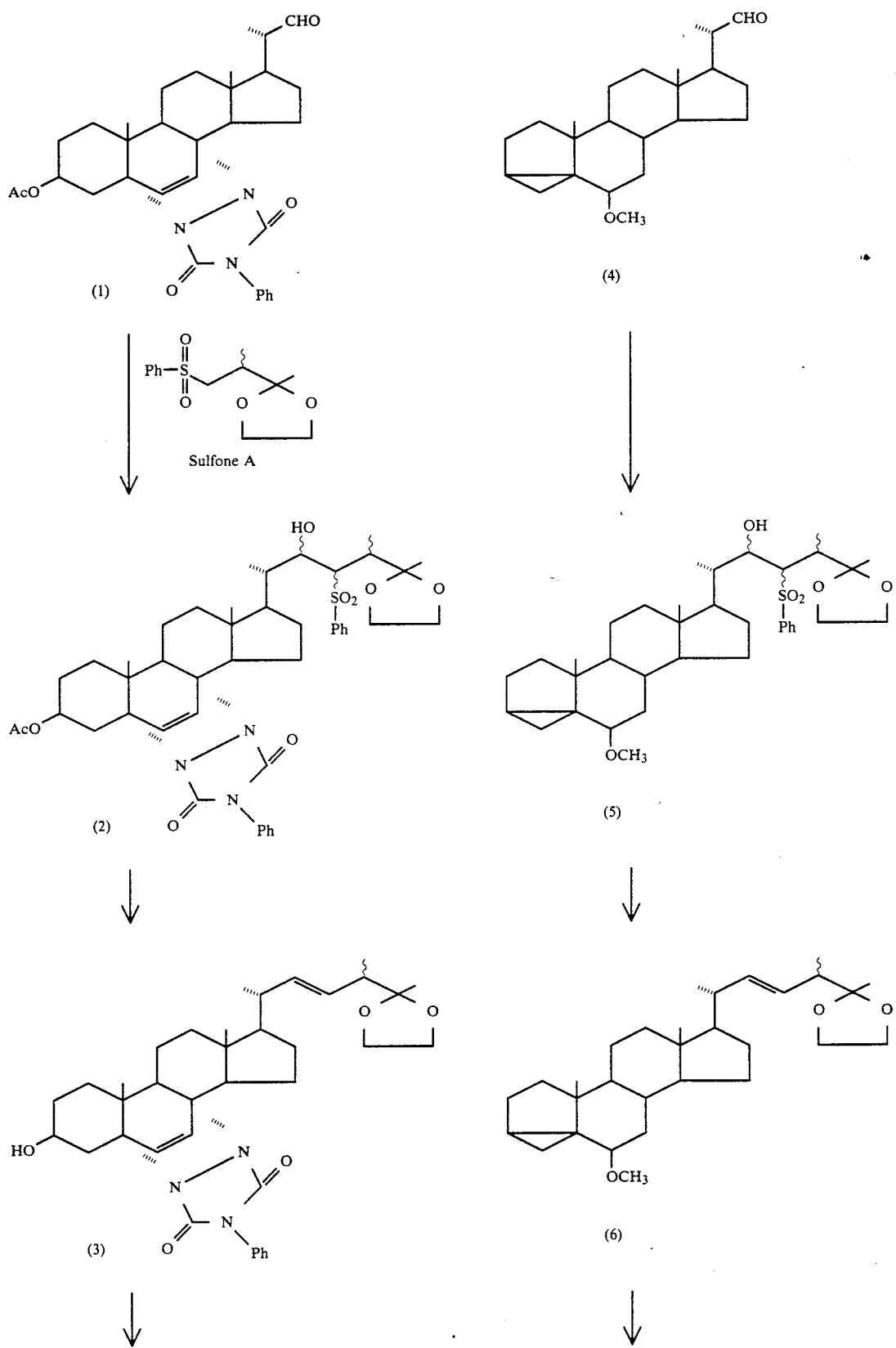

-continued
Process Scheme II

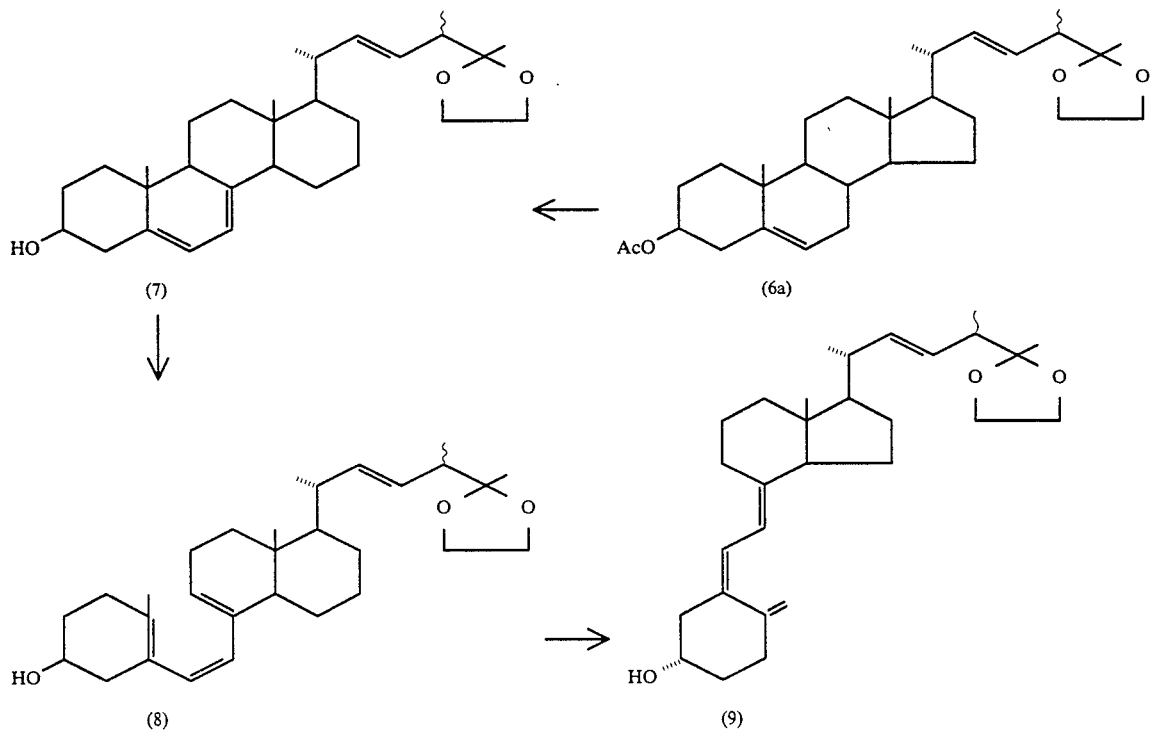

(7)    (6a)

(8)    (9)

Process Scheme III

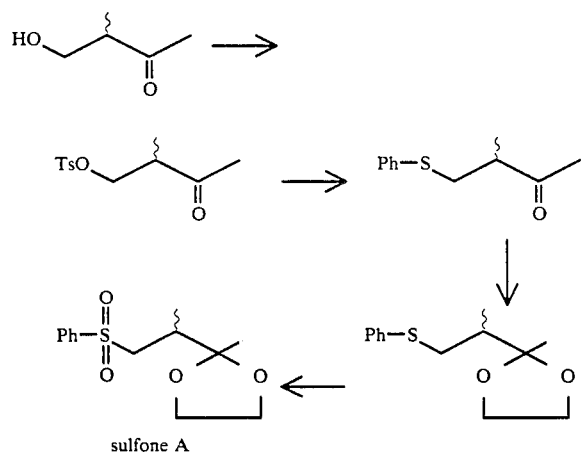

sulfone A

Like the previously known vitamin $D_2$ metabolite, 1 alpha, 25-dihydroxyvitamin $D_2$ (9a), the novel compounds of this invention (i.e. the products of structure 9b, 11a and 11b or their acylated derivatives) exhibit pronounced vitamin D-like activity, and thus represent desirable substitutes for the known vitamin $D_2$ or $D_3$ metabolites in many therapeutic or veterinary applications. The novel compounds may be used for correcting or improving a variety of calcium and phosphate imbalance conditions resulting from a variety of diseases, such as vitamin D-resistant rickets, osteomalacia, hypoparathyroidism, osteo-dystrophy, pseudohypoparathyroidism, osteoporosis, Paget's disease, and similar bone and mineral-related disease states known to the medical practice. The compounds can also be used for the treatment of mineral imbalance conditions in animals, for example, the milk fever condition, poultry leg weakness, or for improving egg shell quality of fowl.

Particularly preferred is 24-epi-1 alpha,25-dihydroxyvitamin $D_2$ (24-epi-1,25-$(OH)_2D_2$) (9b). The compound has the 24-R methyl configuration the configuration which is opposite from that occurring in the natural vitamin $D_2$ metabolite. This compound has been found to possess a unique and unexpected pattern of biological activity which differs from the biological activity pattern of known vitamin D compounds. This activity makes it eminently suitable for the prevention or treatment of physiological disorders in mammals which are characterized by the loss of bone mass.

Specifically, it has been found that although 24-epi-1,25$(OH)_2D_2$ expresses some of the recognized vitamin D-like characteristics affecting calcium metabolism such as increasing intestinal calcium transport, and effecting bone mineralization, it does not increase serum calcium levels of animals on a low calcium diet, even at high dosages. This observed characteristic evinces that the compound upon administration, does not mobilize bone. This combination of properties distinguishes the 24-epi compound from known vitamin D metabolites or analogs (e.g., 1,25$(OH)_2D_3$, 1,25-$(OH)_2D_2$, 1 alpha-OH-$D_3$, and related analogs) which invariably induce both calcium absorption in intestine and mineral mobilization from bone. (See for example, U.S. Pat. No. 3,697,559, U.S. Pat. No. 3,741,996, Reeve et al, Arch. Biochem. and Biophys., Vol. 186, No. 1 (Feb. 1978), pp. 164–167.) This lack of, or minimal bone mobilizing activity of 24-epi-1,25-$(OH)H_2D_2$ along with the ability of the compound to stimulate intestinal calcium absorption and to mineralize bone, indicates that it is an ideal compound for the prevention or treatment of prevalent calcium disorders which are evidenced by loss of bone mass, for example, postmenopausal osteoporosis, involutional osteoporosis, senile osteoporosis and steroid-induced osteoporosis. It will be evident that the compound will find ready application for the prevention or treatment of disease states other than those named, in which the loss of bone mass is an indication. Thus, the compound would be eminently suitable in the treatment of patients undergoing renal dialysis where loss of bone mass as a consequence of the dialysis is encountered.

The following Examples will serve to illustrate the characteristics of 24-epi-1,25-$(OH)_2D_2$ which contribute to its eminent suitability for the prevention or treatment of disease states that evince bone mass loss.

EXAMPLE 15

Figure 2:
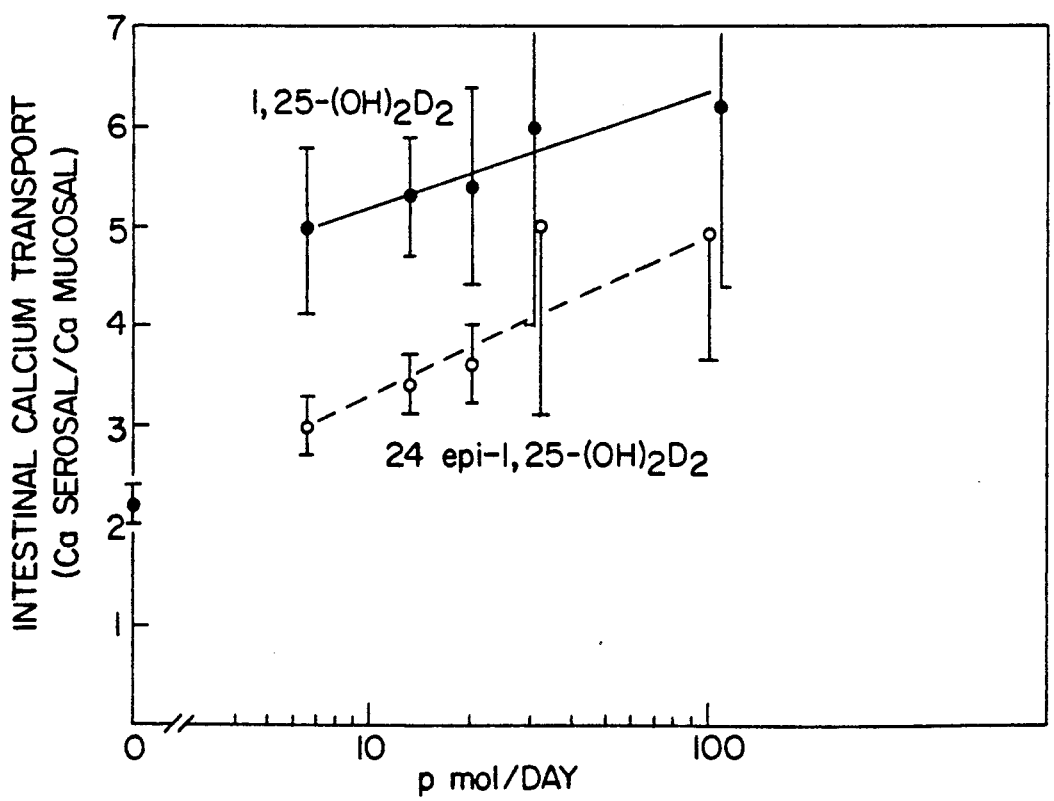

Weanling male rats were placed on the vitamin D deficient diet described by Suda et al., Journal of Nutrition 100, 1049–1052 (1970), modified to contain 0.02% calcium and 0.3% phosphorus. After two weeks on this diet, the animals were given either 1,25-dihydroxyvitamin $D_2$, or 24-epi-1,25-dihydroxyvitamin $D_2$ daily by subcutaneous injection in 0.1 ml of 5% ethanol in propanediol. Twelve hours after the last dose, the animals were killed and the blood calcium and intestinal calcium transport measured. The results of these measurements for the indicated levels of the compounds administered are shown in FIGS. 1 and 2. The intestinal calcium transport measurements shown in FIG. 2 were performed by the method of Martin and DeLuca, American Journal of Physiology 216, 1351–1359 (1969).

EXAMPLE 16

Figure 3:
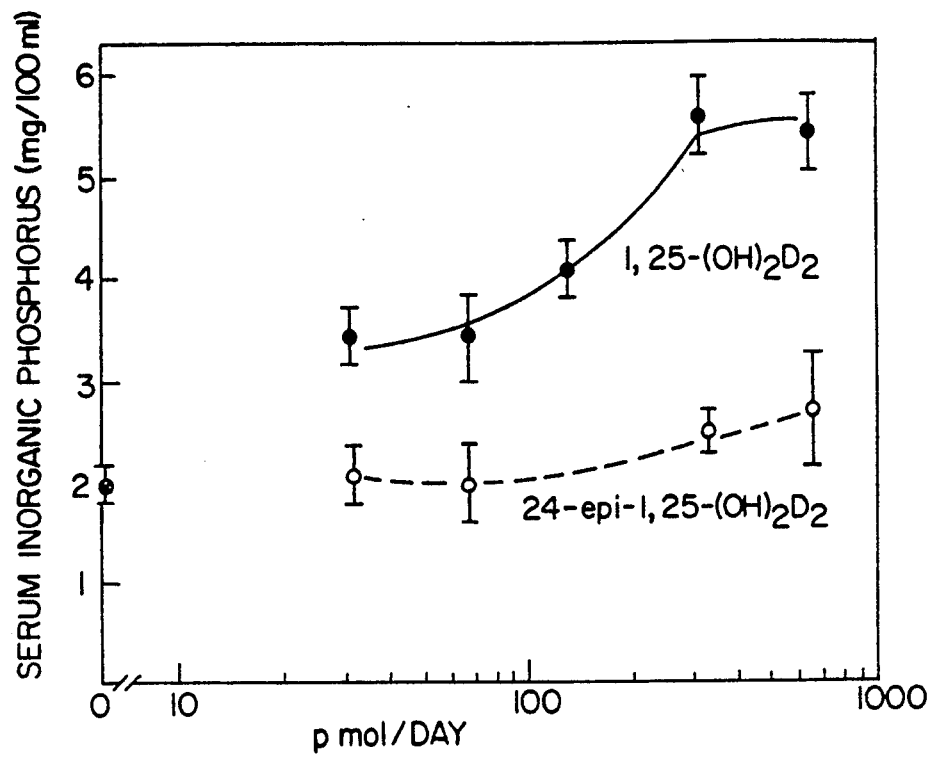

Weanling male rats were placed on a high calcium (1.2% calcium) and low phosphorus (0.1% phosphorus) diet described by Suda et al (supra). The rats were fed this diet for a period of three weeks at which time they were separated into two groups. One group was given 1,25$(OH)_2D_2$ while the other groups was given 24-epi-1,25$(OH)_2D_2$, both in 0.1 ml of 5% ethanol in propane diol subcutaneously at the dosage levels of the compounds shown by the data points in FIG. 3. These doses were continued daily for a period of seven days, at which time the animals were killed and serum inorganic phosphorus determined. Results are shown in FIG. 3.

Figure 4:
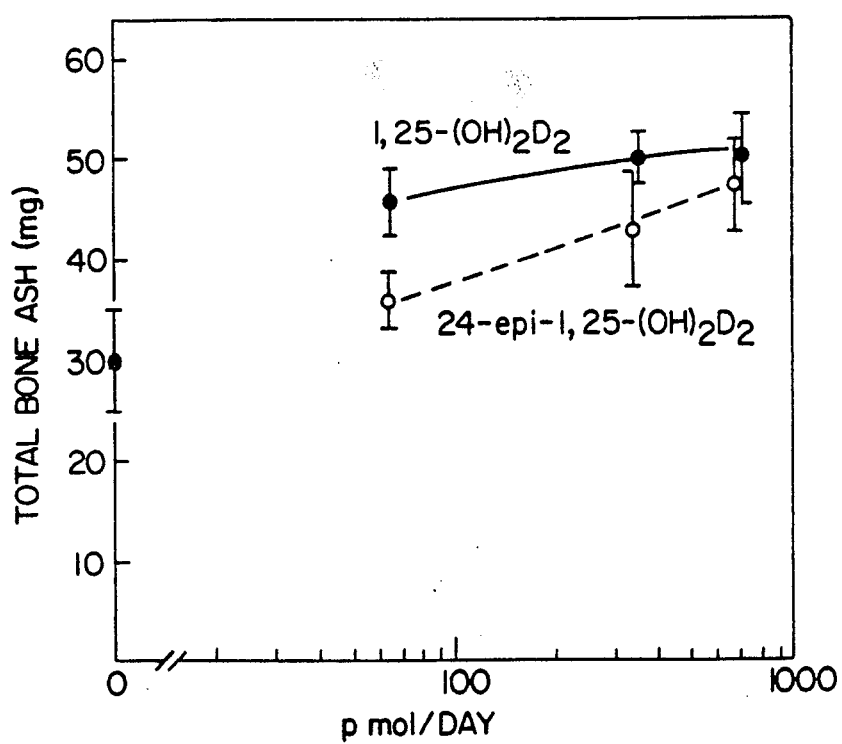

Bone ash was determined by removing the femurs from rats. The femurs were dissected free of adhering connective tissue, extracted for 24 hours in absolute ethanol, and 24 hours in diethyl ether, using a Soxhlet extractor. The bones are ashed at 600° F. for 24 hours. The ash weight was determined by weighing to constant weight. Results are shown in FIG. 4.

The results of the two studies described in Examples 15 and 16, above, illustrate that 24-epi-1,25-$(OH)_2D_2$ is approximately equal in potency to 1 alpha,25-dihydroxyvitamin $D_3$ (1,25-$(OH)_2D_3$) in causing the mineralization of bone and in stimulating intestinal calcium transport. In short, there is no significant difference between the two groups in FIG. 2 and FIG. 4. On the other hand, the elevation of serum inorganic phosphorus which results from mobilization of bone in the case of the low phosphorus diet is very markedly affected by 1,25-$(OH)_2D_2$, but hardly stimulated by 24-epi-1,25$(OH)_2D_2$. Similarly, in the mobilization of calcium from bone, as indicated by the serum calcium levels (FIG. 1) even at the extremely high dose level of about 750 pmoles/day, the 24-epi compound had no effect, while the mobilization effect is evident at much lower doses of 1,25-dihydroxyvitamin $D_2$. Since the rise in serum calcium of rats on a low calcium diet measures the ability to mobilize bone, and since the elevation of blood phosphorus of animals on a low phosphorus diet also measures bone mobilization, these results show that 24-epi-1,25-$(OH)_2D_2$ provides an unexpected property, namely that it is of minimal effectiveness in mobilizing bone calcium, while being fully able to stimulate intestinal calcium transport and the mineralization of new bone, properties which make this compound highly suitable for the treatment of disease states that evince bone loss.

The unique characteristics of 24-epi-1,25-$(OH)_2D_2$, as set forth above, offer the additional opportunity to control the various vitamin D-responsive processes (intestinal calcium absorption, bone mineral mobilization, and bone mineralization) in a manner and to a degree heretofore not feasible. This possibility arises from the fact that the 24-epi compound of this invention may be administered to the mammal either alone (with suitable and acceptable excipients) or in combination with other vitamin D-derivatives which exhibit the full spectrum of D-like activity including the ability to promote a net bone mass gain. By such measures, it is possible therefore to combine (to whatever degree desired) the specificity of action of the 24-epi-analog with the generality of action of other vitamin D metabolites or analogs. Administration of 24-epi-1,25-$(OH)_2D_2$ alone will, as shown above, stimulate intestinal calcium transport and bone mineralization with no or minimal bone mineral mobilization, but the latter activity can be induced by co-administration of one or more of the known vitamin D derivatives (e.g., 1,25-$(OH)_2D_3$, 1 alpha,25-$(OH)_2D_2$, 1 alpha-OH-$D_3$, and related analogs). By adjusting the relative amounts of compounds administered, a degree of control over the relative magnitudes of the intestinal calcium absorption vs. bone mineral mobilization processes can be exercised in a manner not possible with the heretofore known vitamin D derivatives. Co-administration of the 24-epi compound and other vitamin D compounds with bone mobilizing activity or with other hormones which initiate the formation of new bone resorption cavities can be particularly advantageous in situation where some degree of bone mobilization is desired. For example, it is believed that in certain circumstances, bone must first be mobilized before new bone can be laid down. (H. M. Frost "Bone Dynamics in Osteroporosis and Osteomalacic", Henry Ford Hospital Surgical Monograph Series, Charles A. Thomas Co., Springfield, 1966.) In such situations treatment with vitamin D or a vitamin D derivative which will induce bone mobilization, e.g. 1 alpha-hydroxyvitamin $D_3$ or -$D_2$, 1 alpha,25-dihydroxyvitamin $D_3$ or -$D_2$, 25-hydroxyvitamin $D_3$ or -$D_2$, 24,24-difluoro-25-hydroxyvitamin $D_3$, 24,24-difluoro-1 alpha,25-dihydroxyvitamin $D_3$, 24-fluoro-25-hydroxyvitamin $D_3$, 24-fluoro-1 alpha,25-dihydroxyvitamin $D_3$, 2 beta-fluoro-1 alpha-hydroxyvitamin $D_3$, 2 beta-fluoro-25-hydroxyvitamin $D_3$, 2 beta-fluoro-1 alpha, 25-dihydroxyvitamin $D_3$, 26,26,26,27,27,27-hexafluoro-1 alpha, 25-dihydroxyvitamin $D_3$, 26,26,26,27,27,27-hexafluoro-25-hydroxyvitamin $D_3$, 24,25-dihydroxyvitamin $D_3$, 1 alpha, 24,25-trihydroxyvitamin $D_3$, 25,26-dihydroxyvitamin $D_3$, 1 alpha,25,26-trihydroxy- vitamin $D_3$, in combination with 24-epi-1 alpha,25$(OH)_2D_2$ will, by adjustment of the proportions of the 24-epi compound and the bone-mobilizing vitamin D compound in the treatment regimen permit the rate of mineralization of bone to be adjusted to achieve the desired medical and physiological ends.

For therapeutic purposes, the compounds of this invention may be administered orally or by injection or infusion in any form convenient or appropriate to the method of administration selected. Thus, the compounds may be formulated with any therapeutically acceptable and innocuous carrier, in the form of pills, tablets, suppositories or gelatin capsules for oral administration, or they may be formulated as solutions, emulsions, dispersions or suspension in innocuous solvents and oils, and such formulations may contain also other therapeutically active and beneficial constituents, such as other vitamins, salts, sugars, proteins, hormones, etc. as may be appropriate to the specific application. Advantageously, the compounds of this invention are administered, alone or in combination, in dosage amounts of between 0.25 to 100 ug per day. In practice the higher doses are used where therapeutic treatment of a disease state is the desired end while the lower doses are generally used for prophylactic purposes, it being understood, of course, that the specific dosage administered in any given case will be adjusted in accordance with the specific compound administered, the disease to be treated, the condition of the subject and other relevant medical facts that may modify the activity of the drug or the response of the subject, as is well-known by those skilled in the art.

We claim:

1. A compound having the formula

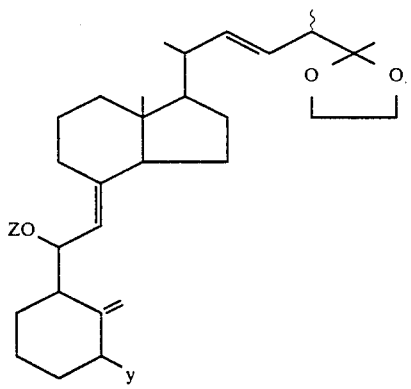

wherein Y is hydrogen, hydroxy or an O-acyl group selected from the group consisting of, an aliphatic acyl group having from 1 to about 6 carbon atoms in all isomeric forms, benzoyl and methyl-halo-or nitro-substituted benzoyl, and residues of dicarboxylic acids having the formulae ROOC $(CH_2)_nCO-$ and ROOCC-$H_2-O-CH_2CO-$ where n is an integer from 0 to 4 and Z is an alkyl group having from 1 to about 6 carbon atoms in any of its isomeric forms.

2. The compounds of claim 1 wherein Y is hydrogen.

3. The compounds of claim 1 wherein Y is hydroxy or O-acetyl.

4. The compound of claim 2 where Z is methyl.

5. The compound of claim 3 where Z is methyl.

6. The compounds of claim 1 where K is an oxygen group.

7. The compounds of claim 6 where K is an ethylenedioxy group.

8. 1 alpha-hydroxy-25-oxo-27-nor vitamin $D_2$ and the acetate thereof.

9. 1 alpha-hydroxy-25-oxo-27-nor-24-epivitamin $D_2$ and the acetate thereof.

10. A compound selected from the group consisting of

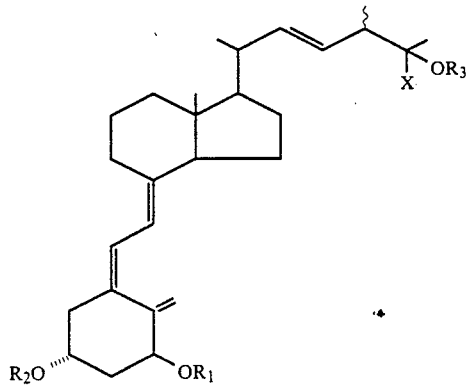

and

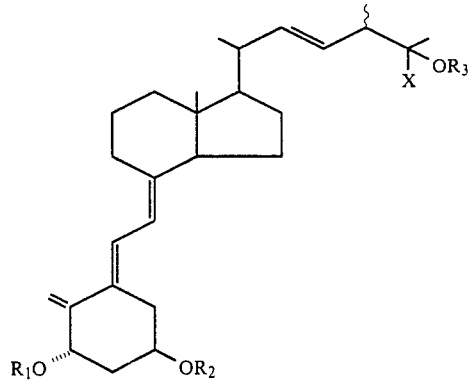

wherein each of $R_1$, $R_2$ and $R_3$ is selected from the group consisting of hydrogen and an acyl group selected from the group consisting of, an aliphatic acyl group having from about 1 to about 6 carbon atoms in all isomeric forms, benzoyl and methyl-, halo-, or nitro-substituted benzoyl, residues of dicarboxylic acids having the formulae ROOC $(CH_2)_nCO-$ and RCOOCC-$H_2-O-CH_2C0-$ n is an integer from) to 4 and wherein X is selected from the group consisting of an alkyl group having from 1 to about 6 carbon atoms, an aryl group selected from the group consisting of phenyl, benzyl and isomeric alkyl-substituted phenyl radicals, and any of such alkyl and aryl groups which have been isotopically labelled, with the proviso that when the C-24 methyl substituent in the 5,6-cis compound has the S- configuration and X is methyl, all of $R_1$, $R_2$, and $R_3$ cannot be hydrogen.

11. The compounds of claim 10 where X is methyl.

12. The compounds of claim 10 where the asymmetric center at C-24 has the (R)-configuration.

13. The compounds of claim 10 where the asymmetric center at C-24 has the (S)-configuration.

14. 1 alpha,25-dihydroxy-24-epivitamin $D_2$.

15. 1 alpha,25-dihydroxy-5,6-trans-24-epi-vitamin $D_2$.

16. A compound selected from the group consisting of

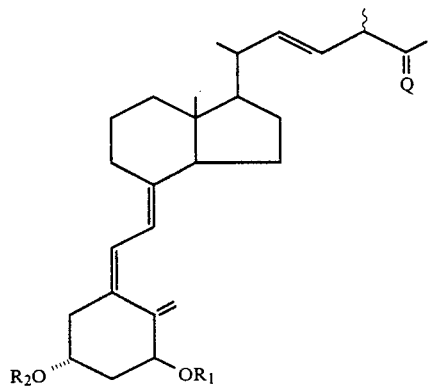
and
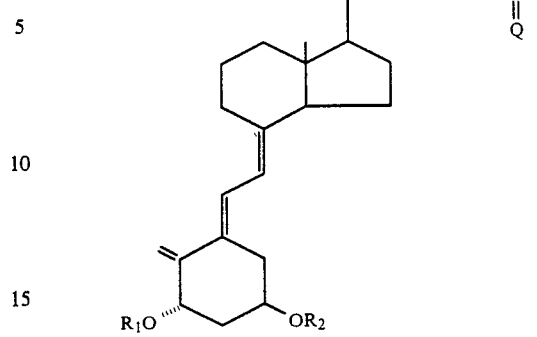
wherein Q is an oxygen or ethylenedioxy group and where $R_1$ and $R_2$, which may be the same or different are hydrogen or acyl.
* * * * *

UNITED STATES PATENT AND TRADEMARK OFFICE
CERTIFICATE OF CORRECTION

PATENT NO. : 5,036,061

DATED : July 30, 1991

INVENTOR(S) : HECTOR F. DeLUCA ET AL

It is certified that error appears in the above-identified patent and that said Letters Patent is hereby corrected as shown below:

Col. 23, line 34-46
The formula in claim 1 should be changed from:

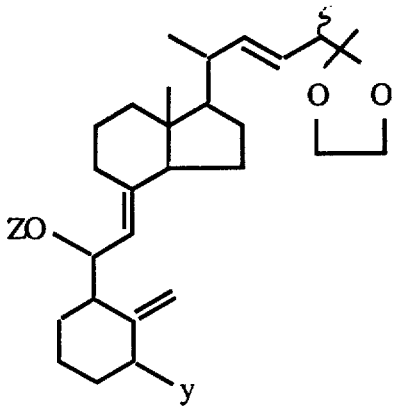

to:

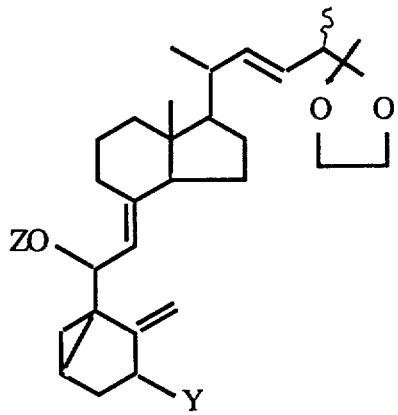

UNITED STATES PATENT AND TRADEMARK OFFICE
CERTIFICATE OF CORRECTION

PATENT NO. : 5,036,061

DATED : July 30, 1991

INVENTOR(S) : HECTOR F. DeLUCA ET AL

It is certified that error appears in the above-identified patent and that said Letters Patent is hereby corrected as shown below:

| | |
|---|---|
| CLAIM 10<br>Column 24, Line 47 | Insert "where" before "n" |
| CLAIM 10<br>Column 24, Line 47 | After "from" delete ")" and substitute therefore --- 1 --- |
| CLAIM 10<br>Column 24, Line 56 | Change "S-" to --- $\underline{S}$- --- |
| CLAIM 12<br>Column 24, Line 61 | Change "(R)" to --- $\underline{(R)}$ --- |
| CLAIM 13<br>Column 24, Line 63 | Change "(S)" to --- $\underline{(S)}$ --- |

Signed and Sealed this

Fifteenth Day of December, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 5,036,061

DATED : July 30, 1991

INVENTOR(S) : HECTOR F. DeLUCA ET AL

It is certified that error appears in the above-identified patent and that said Letters Patent is hereby corrected as shown below:

ON THE COVER SHEET:

add the following item [73]

--- Assignee: Wisconsin Alumni Research Foundation, Madison, Wis. ---

Signed and Sealed this

Twenty-fourth Day of May, 1994

Attest:

BRUCE LEHMAN

Attesting Officer

Commissioner of Patents and Trademarks